US010592067B2

United States Patent
Merdan et al.

(10) Patent No.: US 10,592,067 B2
(45) Date of Patent: Mar. 17, 2020

(54) DISTRIBUTED INTERACTIVE MEDICAL VISUALIZATION SYSTEM WITH PRIMARY/SECONDARY INTERACTION FEATURES

(71) Applicant: Boston Scientific Scimed, Inc., Maple Grove, MN (US)

(72) Inventors: Kenneth Matthew Merdan, Loretto, MN (US); David M. Flynn, Lino Lakes, MN (US); Gregory Ernest Ostenson, St. Paul, MN (US); Benjamin Bidne, Hanover, MN (US); Robbie Halvorson, Plymouth, MN (US); Eric A. Ware, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/671,800

(22) Filed: Aug. 8, 2017

(65) Prior Publication Data

US 2018/0046354 A1 Feb. 15, 2018

Related U.S. Application Data

(60) Provisional application No. 62/374,319, filed on Aug. 12, 2016.

(51) Int. Cl.
*H04N 13/344* (2018.01)
*G06F 3/0481* (2013.01)
(Continued)

(52) U.S. Cl.
CPC .......... *G06F 3/04815* (2013.01); *A61B 5/742* (2013.01); *G06F 3/011* (2013.01);
(Continued)

(58) Field of Classification Search
CPC ............... G06T 19/20; G06T 2210/41; G06T 2219/024; G06T 2219/028; G06T 19/006;
(Continued)

(56) References Cited

U.S. PATENT DOCUMENTS 5,494,042 A 2/1996 Panescu et al.
6,608,628 B1 8/2003 Ross et al.
(Continued)

FOREIGN PATENT DOCUMENTS

CN 106456250 2/2017
DE 102007028065 1/2009
(Continued)

OTHER PUBLICATIONS

International Search Report and Written Opinion for PCT Application No. PCT/US2017/045925 dated Oct. 13, 2017 (10 pages).
(Continued)

*Primary Examiner* — Kimbinh T Nguyen
(74) *Attorney, Agent, or Firm* — Pauly, DeVries Smith & Deffner LLC

(57) ABSTRACT

Embodiments herein relate to distributed interactive medical visualization systems with primary/secondary interaction features and related methods. In an embodiment, a distributed interactive medical visualization system is included. The system can include a first video processing circuit and a first central processing circuit in communication with the first video processing circuit. The system can also include a first communications circuit. The system can also include a primary user interface generated by the first video processing circuit. The primary user interface can include a three-dimensional model of at least a portion of a subject's anatomy from a first perspective, the first perspective configured to be controlled by a primary user. The primary user interface can include a command interface object, wherein
(Continued)

engagement can cause a secondary user interface to begin mirroring the perspective of the primary user on the three-dimensional model of the subject's anatomy. Other embodiments are also included herein.

20 Claims, 9 Drawing Sheets

(51) Int. Cl.

| | | |
|---|---|---|
| G06F 3/01 | (2006.01) | |
| H04N 5/32 | (2006.01) | |
| H04N 13/275 | (2018.01) | |
| A61B 5/00 | (2006.01) | |
| G06F 3/0484 | (2013.01) | |
| G06T 19/20 | (2011.01) | |
| G16H 50/50 | (2018.01) | |
| G06F 19/00 | (2018.01) | |

(52) U.S. Cl.
CPC .......... *G06F 3/04842* (2013.01); *G06T 19/20* (2013.01); *H04N 5/32* (2013.01); *H04N 13/275* (2018.05); *H04N 13/344* (2018.05); *A61B 2576/00* (2013.01); *G06F 19/321* (2013.01); *G06T 2210/41* (2013.01); *G16H 50/50* (2018.01)

(58) Field of Classification Search
CPC .. G06F 19/321; G06F 19/3481; G06F 17/241; H04L 12/1822
See application file for complete search history.

(56) References Cited

U.S. PATENT DOCUMENTS

| | | | |
|---|---|---|---|
| 7,291,166 | B2 | 11/2007 | Cheng et al. |
| 7,840,393 | B1 | 11/2010 | Whirley et al. |
| 8,363,096 | B1 | 1/2013 | Aguirre-Valencia |
| 8,958,615 | B2 | 2/2015 | Blum et al. |
| 9,333,361 | B2 | 5/2016 | Li et al. |
| 9,364,665 | B2 | 6/2016 | Bokil et al. |
| 9,411,935 | B2 | 8/2016 | Moffitt et al. |
| 2003/0212321 | A1 | 11/2003 | Baxter, III |
| 2003/0216710 | A1 | 11/2003 | Hurt |
| 2004/0049115 | A1 | 3/2004 | Murphy et al. |
| 2004/0097805 | A1 | 5/2004 | Verard et al. |
| 2004/0257361 | A1 | 12/2004 | David Tabakman et al. |
| 2006/0100502 | A1 | 5/2006 | Chen et al. |
| 2006/0290695 | A1 | 12/2006 | Salomie |
| 2007/0043466 | A1 | 2/2007 | Vesely et al. |
| 2007/0092864 | A1 | 4/2007 | Reinhardt et al. |
| 2007/0127791 | A1 | 6/2007 | Ernvik et al. |
| 2007/0185485 | A1 | 8/2007 | Hauck et al. |
| 2007/0248261 | A1 | 10/2007 | Zhou et al. |
| 2008/0137926 | A1 | 6/2008 | Skinner et al. |
| 2009/0062642 | A1 | 3/2009 | Hauck |
| 2009/0287186 | A1 | 11/2009 | Adams et al. |
| 2010/0064950 | A1 | 3/2010 | Magaldi |
| 2010/0067768 | A1 | 3/2010 | Ionasec et al. |
| 2010/0094370 | A1 | 4/2010 | Levin et al. |
| 2010/0106475 | A1 | 4/2010 | Smith et al. |
| 2010/0290679 | A1 | 11/2010 | Gasser et al. |
| 2010/0318326 | A1 | 12/2010 | Yamamoto |
| 2011/0170752 | A1 | 7/2011 | Martin et al. |
| 2012/0296392 | A1 | 11/2012 | Lee et al. |
| 2013/0073619 | A1 | 3/2013 | Tumuluri et al. |
| 2013/0128011 | A1 | 5/2013 | Tu et al. |
| 2013/0172732 | A1 | 7/2013 | Kiraly et al. |
| 2013/0234934 | A1* | 9/2013 | Champion ............. G06F 3/012 345/156 |
| 2013/0296845 | A1 | 11/2013 | Bar-Tal et al. |
| 2014/0225887 | A1 | 8/2014 | Aguirre-Valencia |
| 2015/0049081 | A1 | 2/2015 | Coffey et al. |
| 2015/0049082 | A1 | 2/2015 | Coffey et al. |
| 2015/0049083 | A1 | 2/2015 | Bidne et al. |
| 2015/0134031 | A1 | 5/2015 | Moffitt et al. |
| 2015/0347682 | A1 | 12/2015 | Chen et al. |
| 2016/0081658 | A1 | 3/2016 | Perrey et al. |
| 2016/0151634 | A1 | 6/2016 | Carcieri et al. |
| 2016/0225152 | A1 | 8/2016 | Blum et al. |
| 2016/0255086 | A1* | 9/2016 | Vajravelu ............. H04L 63/101 726/4 |
| 2016/0353055 | A1 | 12/2016 | Popescu et al. |
| 2017/0367771 | A1* | 12/2017 | Tako .................... A61B 34/20 |
| 2018/0046355 | A1 | 2/2018 | Merdan et al. |

FOREIGN PATENT DOCUMENTS

| | | |
|---|---|---|
| EP | 2605824 | 6/2013 |
| EP | 2630987 | 8/2013 |
| EP | 2691898 | 2/2014 |
| EP | 2691899 | 2/2014 |
| EP | 2691900 | 2/2014 |
| EP | 2714187 | 4/2014 |
| EP | 2741817 | 6/2014 |
| EP | 2742482 | 6/2014 |
| EP | 2765776 | 8/2014 |
| EP | 2890451 | 7/2015 |
| EP | 2891091 | 7/2015 |
| EP | 3035884 | 6/2016 |
| EP | 2709721 | 9/2016 |
| JP | 2016527994 | 9/2016 |
| WO | 2012024441 | 2/2012 |
| WO | 2012135190 | 10/2012 |
| WO | 2012135191 | 10/2012 |
| WO | 2012135198 | 10/2012 |
| WO | 2012158882 | 11/2012 |
| WO | 2012166656 | 12/2012 |
| WO | 2013023073 | 2/2013 |
| WO | 2013023076 | 2/2013 |
| WO | 2014036079 | 3/2014 |
| WO | 2014036081 | 3/2014 |
| WO | 2015023787 | 2/2015 |
| WO | 2015149042 | 10/2015 |
| WO | 2018031558 | 2/2018 |
| WO | 2018031561 | 2/2018 |

OTHER PUBLICATIONS

International Search Report and Written Opinion for PCT Application No. PCT/US2017/045931 dated Nov. 2, 2017 (13 pages).

"3D Medical Animation Demo—Cardiac Catheterization," Published on Aug. 3, 2012. <https://www.youtube.com/watch?v=hXdNY97Xkmw>.

Brock, Michael "Virtual Reality Among Hottest Tech Tectors to Watch at CES 2016," VR Journal, Jan. 2016 URL <http://vrjournal.com/virtual-reality-among-hottest-tech-sectors-to-watch-at-ces-2016/> (5 pages).

Brugger, Tim "Who's Ready for Virtual Reality? Turns Out, Most Everyone," Fool.com Technology and Telecom Dec. 14, 2015 URL <http://www.fool.com/investing/general/2015/12/14/whos-ready-for-virtual-reality-turns-out-most-ever.aspx?source+eogyholnk0000001&utm_source=yahoo&utm_medium=feed&utm_campaign=article> (4 pages).

Carvalho, Diego D. et al., "Estimating 3D lumen centerlines of carotid arteries in free-hand acquisition ultrasound," International Journal of Computer Assisted Radiology and Surgery, vol. 7, No. 2, Jun. 2011 (9 pages).

Coffey, Dane et al., "Interactive Slice WIM: Navigating and Interrogating Volume Data Sets Using a Multisurface, Multitouch VR Interface," Visualization and Computer Graphics, IEEE Transactions on, vol. 18, pp. 1614-1626, 2012 (13 pages).

Coffey, Dane et al., "Low Cost VR Meets Low Cost Multi-touch," Proceedings of the international Symposium on Visual Computing, Springer Lecture Notes in Computer Science, vol. 6454, pp. 351-360, Nov. 2010 (10 pages).

Coffey, Dane et al., "Slice WIM: A Multi-Surface, Multi-Touch Interface for Overview + Detail Exploration of Volume Datasets in

(56) References Cited

OTHER PUBLICATIONS

Virtual Reality," presented at the Symposium on Interactive 3D Graphics and Games, San Francisco, California, Feb. 2011 (8 pages).
Cohen, Elizabeth "Google Cardboard Saves Baby's Life," CNN video, Jan. 7, 2016 URL <http://www.cnn.com/2016/01/07/health/google-cardboard-baby-saved/index.html>.
"EchoPixel: Hospital Holograms Bring Doctors Into New Era," Bloomberg Mar. 16, 2015 URL <http://www.bloomberg.com/news/videos/2015-03-16/echopixel-hospital-holograms-bring-doctors-into-new-era> (1 page).
Erdman, Arthur G. "Grand Challenge: applying Regulatory Science and Big Data to Improve Medical Device Innovation," IEEE Transactions on Biomedical Engineering, 60(3), pp. 700-706, Mar. 2013 (7 pages).
File History for U.S. Appl. No. 14/459,129 downloaded Sep. 14, 2017 (1244 pages).
File History for U.S. Appl. No. 14/459,163 downloaded Sep. 14, 2017 (1525 pages).
File History for U.S. Appl. No. 14/459,202 downloaded Sep. 14, 2017 (1513 pages).
File History for European Patent Application No. 14758043.5 downloaded Sep. 14, 2017 (455 pages).
"First-in-man use of virtual reality imaging in cardiac cath lab to treat blocked coronary artery," Elsevier Health Sciences, Nov. 20, 2015 URL <Http://www.eurekalert.org/pub_releases/2015-11/ehs-fuo111815.php#.Vo1R81ipUAk.mailto> (3 pages).
Fornell, Dave "Editor's Choice of Most Innovative New Technology at RSNA 2015," Diagnostic and Interventional Cardiology Dicardiology.com 2015 URL <http://www.dicardiology.com/videos/editors-choice-most-innovative-new-technology-rsna-2015> (1 page).
Gruber, Ben "Body Parts Floating in 3D Space to Give Medicine Virtual Shape," Thomson Reuters Science News Sep. 21, 2015 URL <http://www.reuters.com/article/us-usa-virtual-medicine-tracked-idUSKCN0RL1W320150921> (3 pages).
"Hp Zvr 23.6-inch Virtual Reality Display (K5H59A8)," HP Product Overview 2015 URL <http://www8.hp.com/us/en/products/monitors/product-detail.html?oid=7445887&jumpid=reg_r1002_usen_c-001_title_r0001#!tab=features> (2 pages).

"International Preliminary Report on Patentability," for International application No. PCT/US2014/050944 dated Feb. 16, 2016 (12 pages).
"International Search Report and Written Opinion," for International application No. PCT/US2014/050944 dated Feb. 19, 2015 (19 pages).
"Kinect Sensor Allows Surgeons to Manipulate 3D CT Images in Midair," Published Feb. 11, 2011. <https://www.youtube.com/watch?v=id7OZAbFaVI>.
"Stratasys and Vital Images Partner on 3-D Printing," Diagnostic and Interventional Cardiology Dicardiology.com Dec. 14, 2015 URL<http://www.dicardiology.com/product/stratasys-and-vital-images-partner-3-d-printing> (2 pages).
Tilley, Aaron "HP Inc. Is Bringing Its Giant Virtual Reality Display Into Healthcare," Forbes Tech, Dec. 13, 2015 URL <http://www.forbes.com/sites/aarontilley/215/12/03/hp-inc-is-bringing-its-giant-virtual-reality-display-into-the-operating-room/> (2 pages).
"Video: Cardiology Medical Animation—Deployment of Mitral Valve Clip," Published on Jun. 26, 2009, scientificanim777. URL <https://www.youtube.com/watch?v=yET7if-tLtM> (15 pages).
Non-Final Office Action for U.S. Appl. No. 15/671,873 dated Oct. 4, 2018 (24 pages).
Final Office Action for U.S. Appl. No. 15/671,873 dated Feb. 13, 2019 (23 pages).
International Preliminary Report on Patentability for PCT Application No. PCT/US2017/045925 dated Feb. 21, 2019 (7 pages).
International Preliminary Report on Patentability for PCT Application No. PCT/US2017/045931 dated Feb. 21, 2019 (10 pages).
Response to Non-Final Rejection dated Oct. 4, 2018, for U.S. Appl. No. 15/671,873, submitted via EFS-Web on Nov. 26, 2018, 10 pages.
"Non-Final Office Action," for U.S. Appl. No. 15/671,873 dated Jul. 17, 2019 (20 pages).
"Response to Final Rejection," dated Feb. 13, 2019, for U.S. Appl. No. 15/671,873 submitted via EFS-Web on May 6, 2019, 10 pages.
"Response to Final Rejection," dated Feb. 13, 2019 and Advisory Action dated May 21, 2019, for U.S. Appl. No. 15/671,873, submitted via EFS-Web on Jun. 12, 2019, 10 pages.

* cited by examiner

DISTRIBUTED INTERACTIVE MEDICAL VISUALIZATION SYSTEM WITH PRIMARY/SECONDARY INTERACTION FEATURES

This application claims the benefit of U.S. Provisional Application No. 62/374,319, filed Aug. 12, 2016, the contents of which are herein incorporated by reference in its entirety.

FIELD

Embodiments herein relate to distributed interactive medical visualization systems with primary/secondary interaction features and related methods.

BACKGROUND

Medical diagnosis and treatment is often aided by, or in some cases based upon, visual observation of one or more portions of a patient's anatomy. Most commonly, this visual observation is performed through direct physical observation of what is visible to the clinician with the unaided eye. In surgical scenarios, this may include visual observation of internal organs.

Various instruments have been configured with optics or electronic imaging cameras to allow visual observation of portions of the patient's anatomy that may otherwise be difficult to see. By way of example, bronchoscopes, endoscopes, and the like have all allowed clinicians to visually observe portions of the anatomy that are otherwise hidden.

Techniques for medical imaging have also greatly extended the ability of clinicians to visually observe portions of a patient's anatomy. Beginning with techniques such as x-ray radiography, and later including techniques such as fluoroscopy, computerized axial tomography (CAT), and magnetic resonance imaging (MRI), the ability to view portions of a patient's anatomy has never been greater. However, in many cases, the images generated by medical imaging systems are two-dimensional and thus require a great degree of skill in order to interpret properly. Some imaging systems provide images that include three-dimensional information, but are rendered on two-dimensional displays causing much of the value of the three-dimensional information to be lost.

SUMMARY

Embodiments herein include distributed interactive medical visualization systems with primary/secondary interaction features and related methods. In first aspect, a distributed interactive medical visualization system is included having a first video processing circuit and a first central processing circuit in communication with the first video processing circuit. The system can also include a first communications circuit in communication with the first central processing circuit. The system can also include a primary user interface generated by the first video processing circuit. The primary user interface can include a three-dimensional model of at least a portion of a subject's anatomy from a first perspective, the first perspective configured to be controlled by a primary user. The primary user interface can further include a command interface object, wherein engagement of the command interface object causes a secondary user interface to begin mirroring the perspective of the primary user on the three-dimensional model of the subject's anatomy.

In addition to one or more of the preceding or following aspects, or in the alternative to some aspects, in a second aspect the three-dimensional model can include one or more of patient data gathered in real-time, previously stored patient data, and idealized model data.

In addition to one or more of the preceding or following aspects, or in the alternative to some aspects, in a third aspect information about the current perspective of a primary user is broadcast across a network.

In addition to one or more of the preceding or following aspects, or in the alternative to some aspects, in a fourth aspect information about the current perspective of a secondary user is broadcast across a network.

In addition to one or more of the preceding or following aspects, or in the alternative to some aspects, in a fifth aspect the first video processing circuit is co-located with a machine displaying the primary user interface.

In addition to one or more of the preceding or following aspects, or in the alternative to some aspects, in a sixth aspect the first video processing circuit is remotely located from a machine displaying the primary user interface.

In addition to one or more of the preceding or following aspects, or in the alternative to some aspects, in a seventh aspect engagement of the command interface object causes the primary user interface to display a three-dimensional model of the subject's anatomy from a perspective of a secondary user in a mirrored fashion wherein the secondary user can change the perspective of the three-dimensional model of the subject's anatomy.

In addition to one or more of the preceding or following aspects, or in the alternative to some aspects, in an eighth aspect a distributed interactive medical visualization system is included having a first video processing circuit and a first central processing circuit in communication with the first video processing circuit. The system can also include a first communications circuit in communication with the first central processing circuit. The system can also include a primary user interface generated by the first video processing circuit. The primary user interface can include a three-dimensional model of at least a portion of a subject's anatomy from a first perspective, the first perspective configured to be controlled by a primary user. The user interface can also include one or more graphical representations of one or more secondary users who are viewing the same three or more dimensional graphical representation wherein each of the one or more graphical user representations are not visible to the one or more secondary users.

In addition to one or more of the preceding or following aspects, or in the alternative to some aspects, in a ninth aspect a distributed interactive medical visualization system is included having a first video processing circuit and a first central processing circuit in communication with the first video processing circuit. The system can also include a first communications circuit in communication with the first central processing circuit. The system can also include a primary user interface generated by the first video processing circuit. The system can also include one or more secondary user interfaces generated by one or more secondary video processing circuits, each of the secondary user interfaces including a three-dimensional model of at least a portion of a subject's anatomy from a first perspective. The primary user interface can further include a command function object, wherein selection of one or more secondary users and engagement of the command function object causes a user-group to be formed. The primary user interface can allow the primary user to specify interface settings at a group-level for a selected user group.

In addition to one or more of the preceding or following aspects, or in the alternative to some aspects, in a tenth aspect a distributed interactive medical visualization system is included having a first video processing circuit and a first central processing circuit in communication with the first video processing circuit. The system can also include a first communications circuit in communication with the first central processing circuit. The system can also include a primary user interface generated by the first video processing circuit. The primary user interface can include a three-dimensional model of at least a portion of a subject's anatomy from a first perspective, the first perspective configured to be controlled by a primary user. The primary user interface can further include a command function object, wherein engagement of the command interface object allows the primary user to select one out of a group of secondary users, wherein the selected secondary user gains the ability to direct the perspective on the three-dimensional model viewed by the primary user and the other secondary users.

In addition to one or more of the preceding or following aspects, or in the alternative to some aspects, in a eleventh aspect a distributed interactive medical visualization system is included having a first video processing circuit and a first central processing circuit in communication with the first video processing circuit. The system can also include a first communications circuit in communication with the first central processing circuit. The system can also include a primary user interface generated by the first video processing circuit. The primary user interface can include a three-dimensional model of at least a portion of a subject's anatomy from a first perspective, the first perspective configured to be controlled by a primary user. The primary user interface can further include a command function object, wherein engagement of the command interface object allows the primary user to create a communication for one or more secondary users to be displayed on one or more secondary user interfaces.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
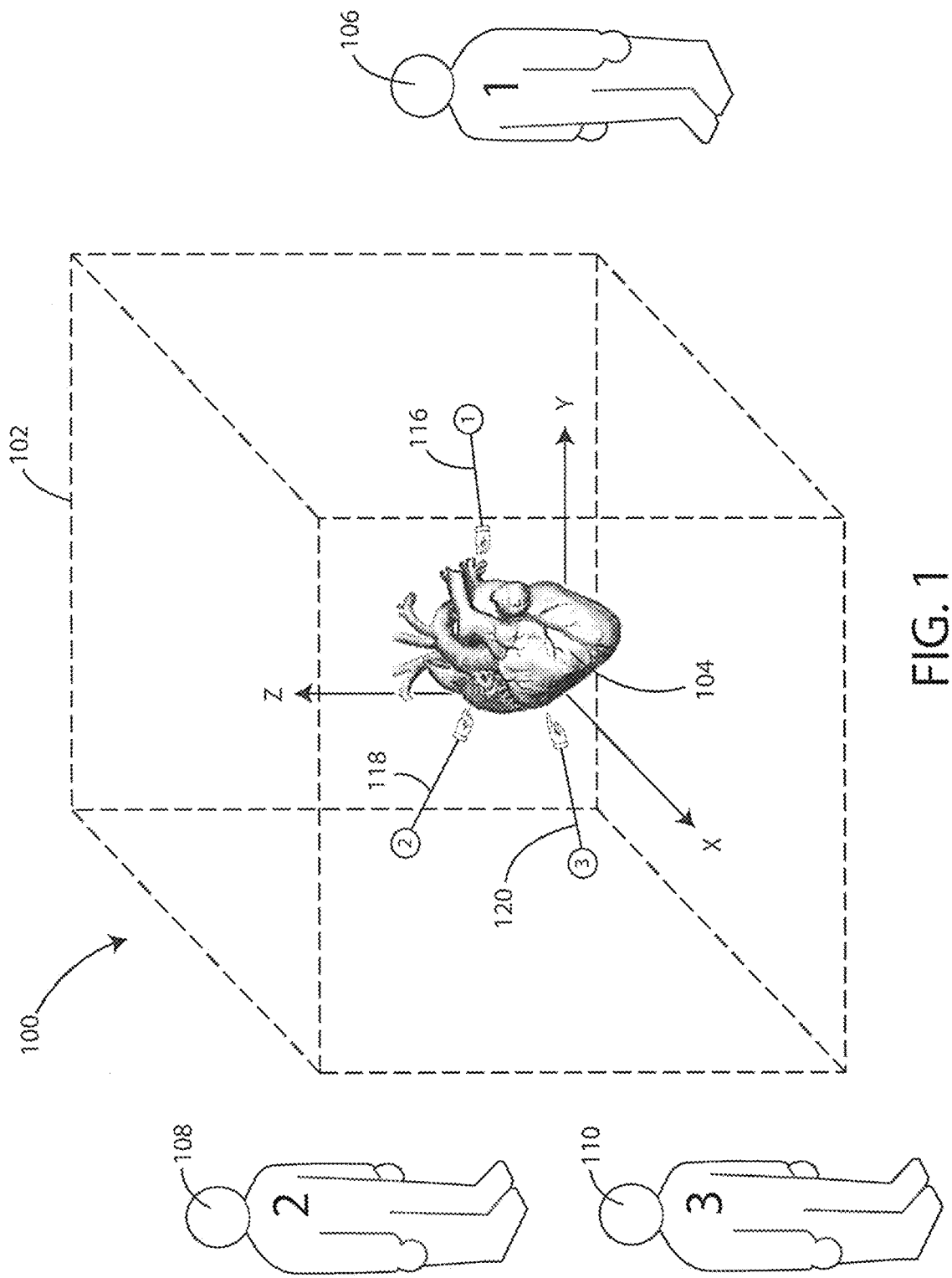
FIG. 1 is a schematic view of aspects of a distributed interactive medical visualization system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

There are many techniques by which visual anatomical data can be gathered. Techniques can include x-ray radiography, fluoroscopy, computerized axial tomography (CAT), magnetic resonance imaging (MRI), and the like. Traditionally, one challenge in using such information has been that images generated are commonly two-dimensional and require a great degree of skill in order to interpret properly. Some imaging systems provide images that include three-dimensional information, but are rendered on two-dimensional displays causing much of the value of the three-dimensional information to be lost.

Various newer techniques allow for three-dimensional image data to be displayed in a way that appears to the user to reflect three-dimensions. While the techniques vary, they are typically based on the fundamental principle of displaying slightly different images to each eye of the user, allowing the sensation of a three-dimensional image to be experienced by the system user. Display of visual information in three dimensions is a great step forward in allowing users to rapidly learn based on what they are seeing.

Systems and methods for allowing multiple individuals (users) to interact with the same three-dimensional image model at the same time are provided herein. In many scenarios, allowing multiple individuals to interact with the same three-dimensional image model at the same time provides unique benefits. For example, in a teaching scenario, allowing a primary user (such as a teacher or leader) to interact with a three-dimensional anatomical model at the same time as one or more secondary users (such as students or followers) can allow the primary user to convey more information related to the anatomical model than would otherwise be possible. In addition, by experiencing the visualization in three-dimensions, the one or more secondary users can increase their rate of learning.

Referring now to FIG. 1, a schematic view is shown of aspects of a distributed interactive medical visualization system 100 in accordance with various embodiments herein. The distributed interactive medical visualization system 100 can include a three-dimensional model 102 of at least a portion of a subject's anatomy 104. The three-dimensional model 102 can extend in the X, Y and Z dimensions. Multiple individuals can interface with the three-dimensional model 102 simultaneously. For example, a primary user 106 can be viewing and interacting with the three-dimensional model 102 at the same time as one or more secondary users 108, 110. In some embodiments, each user can be viewing the model 102 from their own perspective. By way of example, the primary user 106 can be viewing the model 102 from a first perspective 116, while a first secondary user 108 can be viewing the model 102 from a second perspective 118 and a second secondary user 110 can be viewing the model 102 from a third perspective 120.

The perspective of each individual user interacting with the model 102 can be defined in various ways. In some embodiments, an individual perspective can include coordinates indicating the point of origin for the individual user's view or vision. This allows the user to "move" through the model as their point of origin changes. In some embodiments, an individual perspective can also include angles indicating the direction that the user is currently looking from their point of origin.

Figure 2:
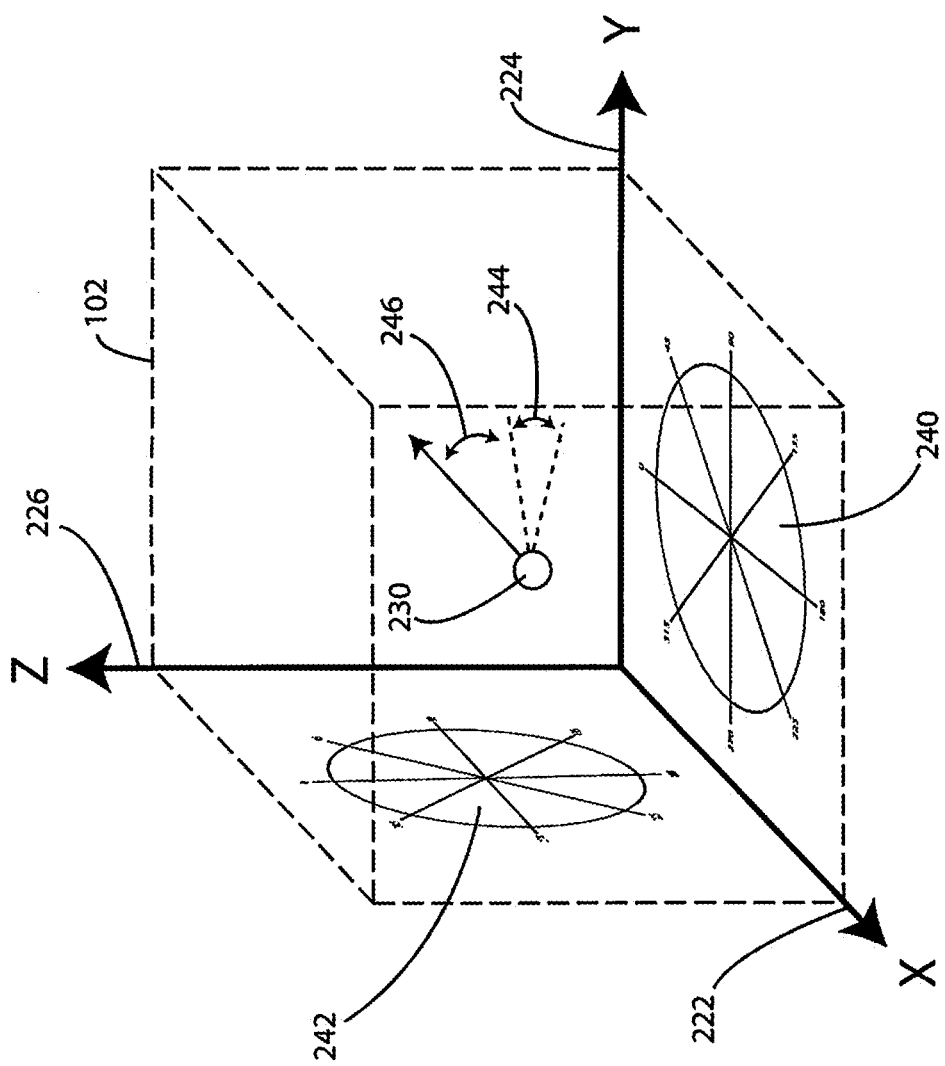
FIG. 2 is a schematic view of a three-dimensional model illustrating an embodiment of a particular user's perspective in accordance with various embodiments herein.

Referring now to FIG. 2, a schematic view is shown of a three-dimensional model 102 illustrating an embodiment of a particular user's perspective. In some embodiments, the particular user's perspective can include a location and a viewing angle. For example, the model can include X (222), Y (224), and Z (226) dimensions. The total volume of the model can be a matter of the product of the maximum magnitude of each of the X, Y and Z dimensions. An individual's perspective can include a location (or point of origin) within the maximum X, Y and Z bounds. For example, point of origin 230 can represent a particular individual's current position within the three-dimensional model. In order to represent a particular user's perspective, the model can also take into account viewing angles. For example, by using a first angle 240 reflective of rotation within the XY plane and a second angle 242 reflective of rotation within the Z plane it is possible to specify any possible directional view within the model 102. As such, a user's perspective can be defined by the point of origin 230, in combination with the XY angle 244 and the Z axis angle 246. While this provides one example of how a user's perspective within a three-dimensional model can be defined, it will be appreciated that there are many other possible ways to precisely describe the user's perspective.

Figure 3:
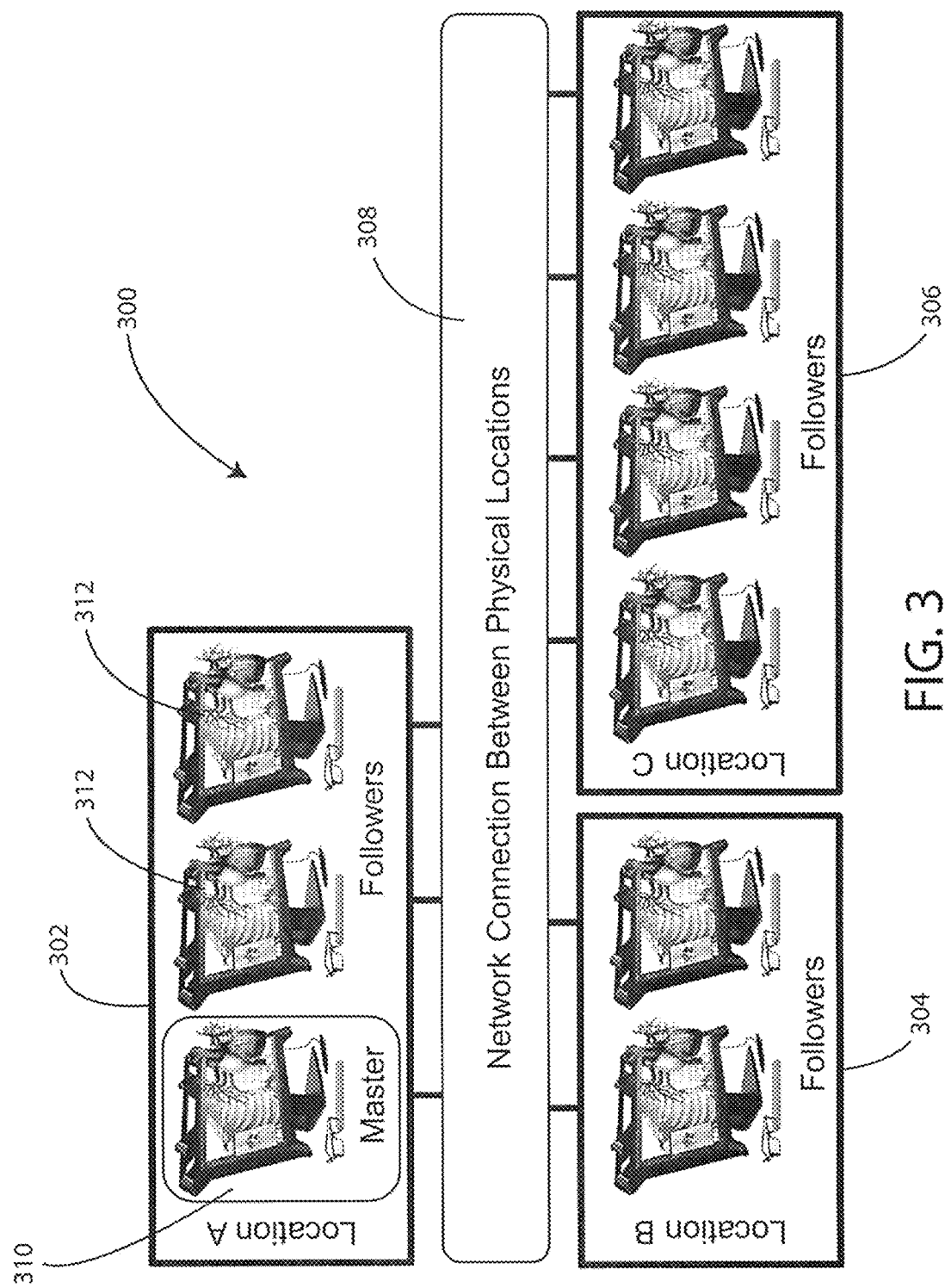
FIG. 3 is a schematic diagram of a distributed interactive medical visualization system in accordance with various embodiments herein.

Interactive medical visualization systems can be "distributed" in that they can be physically distributed across multiple individual machines or workstations. The individual machines or workstations can be in the same physical location or area or they can be in separate physical locations. Referring now to FIG. 3, a schematic diagram is shown of a distributed interactive medical visualization system 300 in accordance with various embodiments herein. In this example, the visualization system 300 includes users in a first location 302 (location A), a second location 304 (location B), and a third location 306 (location C). In some embodiments, the different physical locations may simply be different rooms in the same facility, such as a hospital or a university. In other embodiments, the different physical locations may be miles apart from one another. The locations (302, 304 and 306) can be interconnected via a network connection 308 existing between the disparate physical locations. In this view, the first location 302 includes a master user 310 (or primary user or leader) and two followers 312 (or secondary users). The other locations include only followers. It will be appreciated, however, that in some cases the master user 310 can be in a physical location by themselves. In still other cases, all of the users may be in the same physical location. In some scenarios there may be more than one master user.

The architecture of interactive medical visualization systems herein can vary. In some embodiments, the system can exist in a peer-to-peer type model without a central node or controlling machine. In other embodiments, the system can include a central node, such as an anatomical model server that calculates aspects about the three-dimensional model and various users currently in the model and then sends this information on to individual machines or workstations for rendering. In still other embodiments, video rendering can occur almost entirely on a central node or server (or cluster of servers) and video images can then be pushed to individual workstations which display received video signals (encoded or non-encoded) and which receive and transmit user input.

Figure 4:
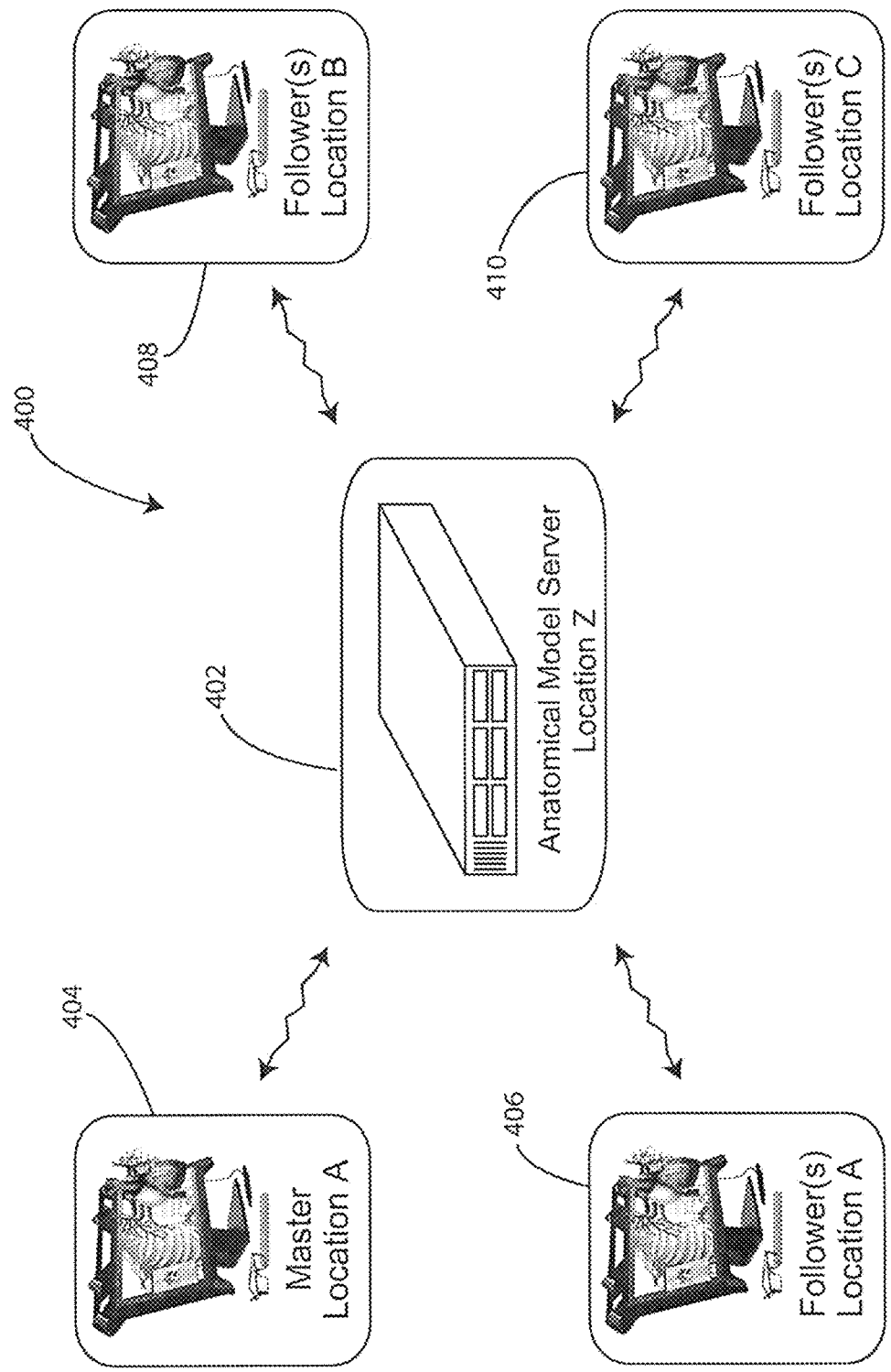
FIG. 4 is a schematic view of a distributed interactive medical visualization system in accordance with various embodiments herein.

Referring now to FIG. 4, a schematic view is shown of a distributed interactive medical visualization system 400 in accordance with various embodiments herein. The system 400 includes a master user 404 (or leader or primary) at location A in bidirectional communication with an anatomical model server 402 at location Z. Location Z can be the same or different than location A. The system 400 also include a follower 406 at location A, a follower 408 at location B, and a follower 410 at location C. In some embodiments, substantial video processing, including but not limited to image or video rendering, occurs on the anatomical model server 402 and video streams are then distributed to individual user nodes. In other embodiments, the anatomical model server 402 serves primarily only to coordinate the interaction between users and the majority of video processing occurs at the level of individual nodes (machines operated by individual users) of the system.

Each individual machine or system can provide or display a user interface for individuals to interface with. The user interface can be generated by a video processing circuit (discussed in greater detail below). The video processing circuit can be local to the user's machine or can be located at a central node or server. The user interface can include various features. By way of example, the user interface can include a representation of the three-dimensional model of at least a portion of a subject's anatomy from a certain perspective. In some cases, the perspective can be configured to be controlled by the system user (primary or secondary) through the user interface.

The user interface can include various command interface objects. Command interface objects can include various elements that a user can interact with either directly (such as with a touch screen) or indirectly (such as with a keyboard, a mouse, a pen, or the like either real or virtual). Command interface objects can include, but are not limited to, a button, a menu tree, a slider bar, a dial, or the like. Engagement or actuation of the command interface object by the user can cause various actions or functions to be executed as described in greater detail below.

Figure 5:
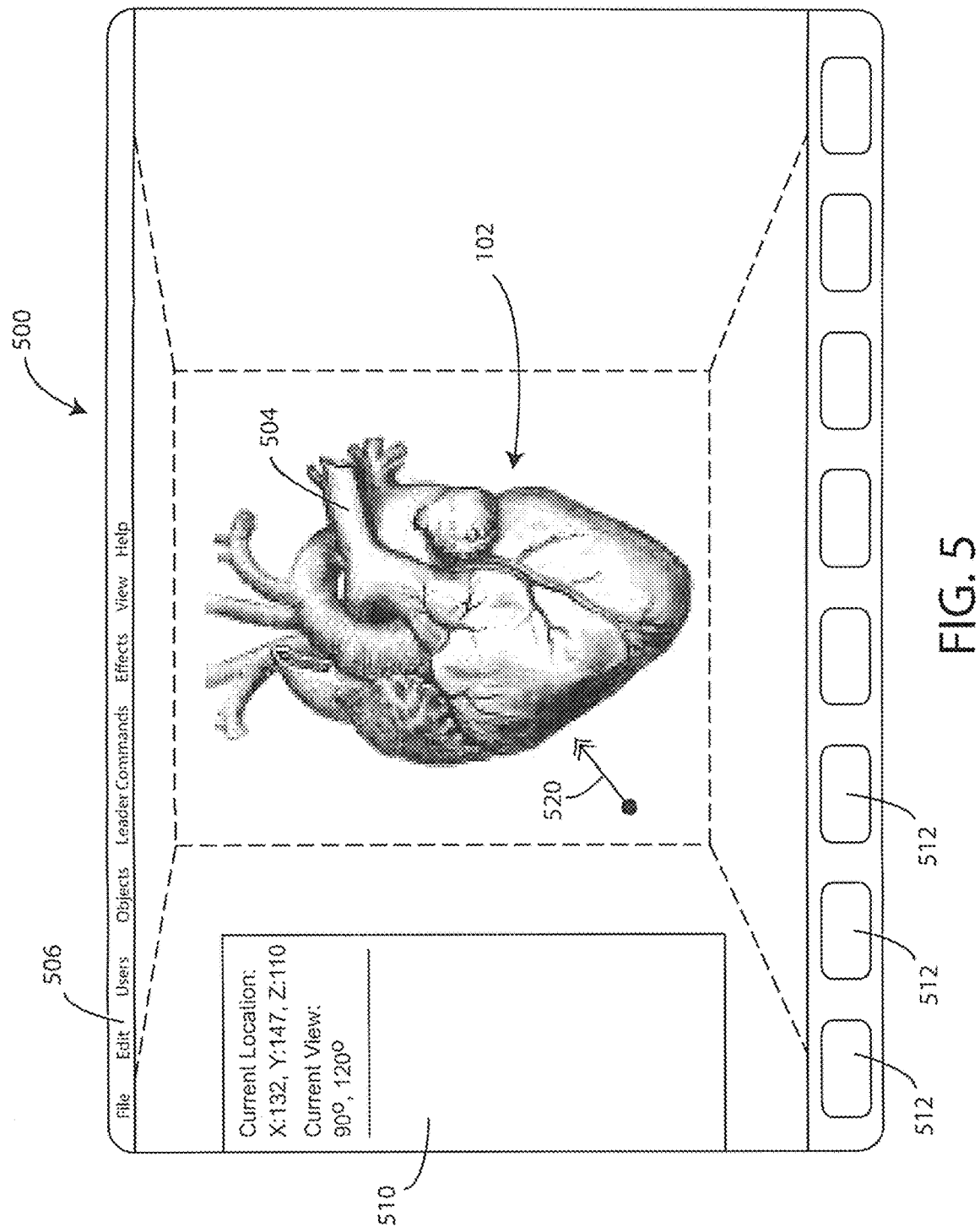
FIG. 5 is a schematic view of an exemplary user interface shown in accordance with various embodiments herein.

Referring now to FIG. 5, a schematic view of an exemplary user interface 500 is shown in accordance with an embodiment herein. The user interface 500 includes a three-dimensional anatomical model 102. The anatomical model 102 includes a three-dimensional image 504 of at least a portion of a patient's anatomy. The user interface can show an icon or other graphical object 520 indicating the position and/or view of another user interacting with the same three-dimensional anatomical model 102.

The user interface 500 can also include a menu bar 506 that can include command interface objects such as menu trees. The user interface 500 can also include one or more command interface objects such as buttons 512. In some embodiments, the user interface 500 can also include an information side bar 510. The information side bar 510 can be selectively shown or hidden and can display information such as the current location and current view of the user interacting with the user interface or information for another selected user. For example, if the user of the system displaying the user interface 500 clicks on the graphical object 520 indicating another user, then that user's information can be displayed in the side bar 510. In some embodiments, instead of a side bar, the same types of information can be displayed on a bar attached to the bottom or top of the screen. In still other embodiments, the same types of information can be rendered within the three-dimensional model itself.

The three-dimensional anatomical model can include various other types of graphical elements rendered to be within the model or portion of the user interface. By way of example, the three-dimensional model can include graphical representations of one or more other users and their respective positions and current views. In addition, objects such as medical devices can be superimposed and/or rendered in the three-dimensional model.

Figure 6:
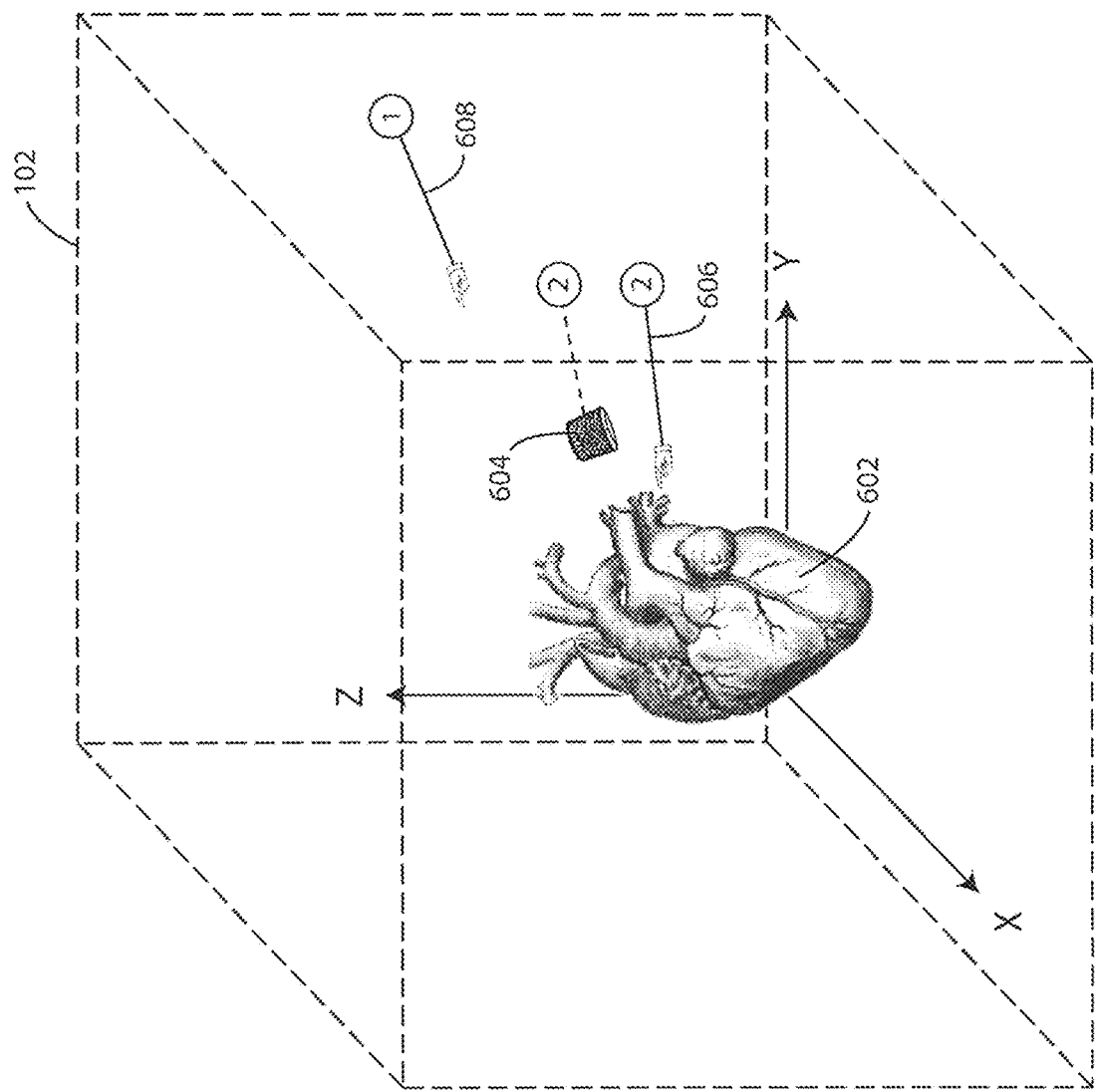
FIG. 6 is a schematic view of a three-dimensional anatomical model in accordance with various embodiments herein.

Referring now to FIG. 6, a schematic view is shown of a three-dimensional anatomical model in accordance with various embodiments herein. The three-dimensional anatomical model can include a visual representation of at least a portion of a patient's anatomy 602. The three-dimensional anatomical model can include a visual representation of a medical device 604. In this case, the medical device 604 is a heart valve. However, it will be appreciated that the medical device can be any sort of medical device including, but not limited to, a stent, an implantable cardiac rhythm management device, a catheter, an embolic protection device, and the like. The user can manipulate the medical device including moving, spinning, and/or deploying the medical device. In this view, the perspective of a first user 608 is shown along with the perspective of a second user 606.

As described above, the three-dimensional model can include a view of at least a portion of a patient's anatomy. In addition, the three-dimensional model can include other aspects including representations of medical devices, indications of other users, and general information superimposed into the model. The anatomical visualization can include portions of data from various sources. By way of example, the anatomical visualization can include live visualization data taken from a patient in real-time, visualization data previously recorded from a patient and stored, as well as idealized anatomical model data drawn from general medical knowledge and/or from a population of patients. In some cases, the system can blend portions of data from one or more of these sources in order to create the three-dimensional anatomical model used in various embodiments herein.

Figure 7:
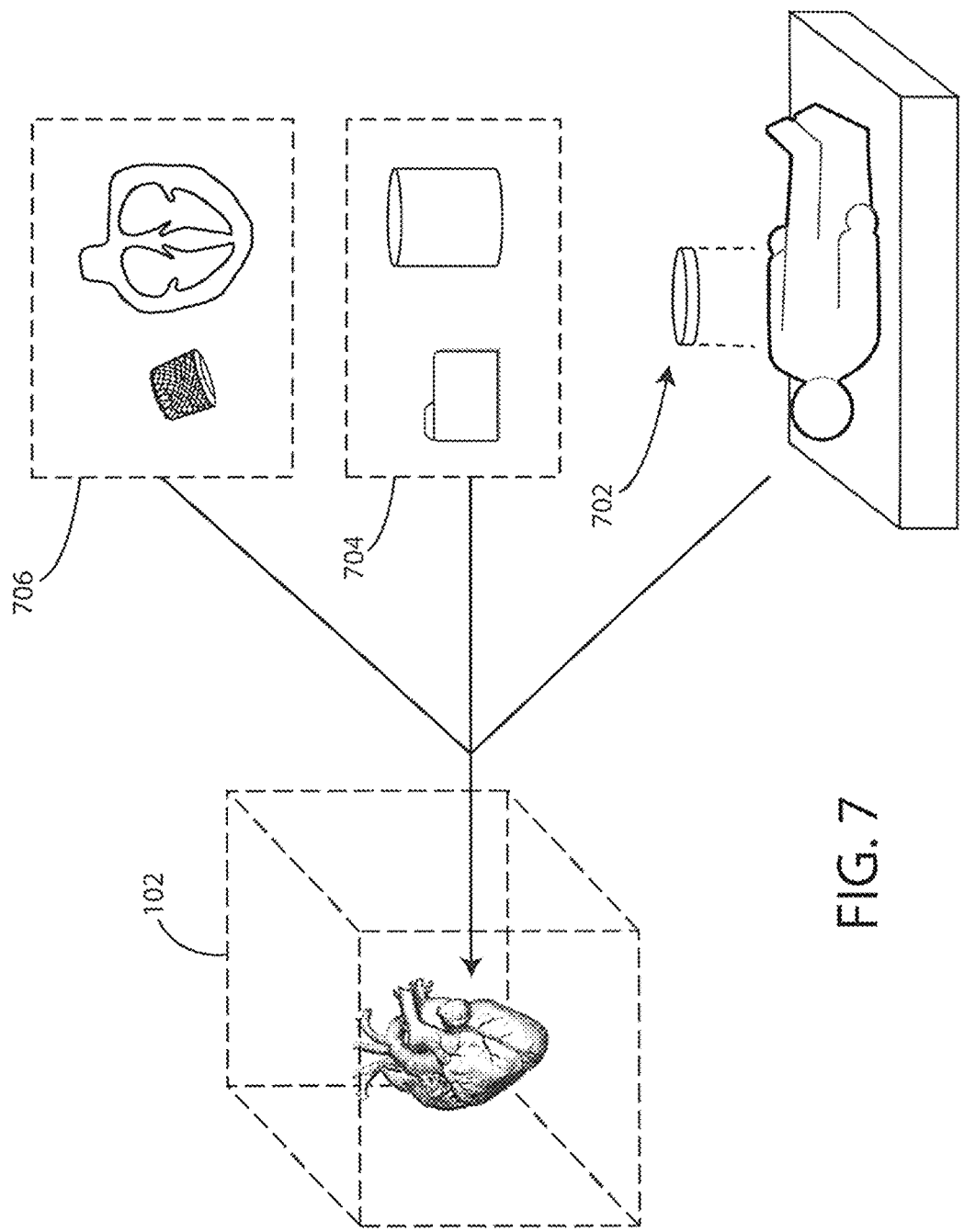
FIG. 7 is a schematic view showing sources of data for use in generating a three-dimensional anatomical model.

Referring now to FIG. 7, a schematic view is shown indicating sources of data for use in generating a three-dimensional anatomical model 102. The sources of data can include patient data gathered in real-time 702, previously stored patient data 704 (such as data stored in files, folders, and/or databases), and idealized model data 706. Patient data gathered in real-time can include data such as medical imaging data including, but not limited to, x-ray radiography data, fluoroscopy data, computerized axial tomography (CAT) data, magnetic resonance imaging (MRI) data, camera data, and the like. Previously stored patient data can include data such as medical imaging data including, but not limited to, x-ray radiography data, fluoroscopy data, computerized axial tomography (CAT) data, magnetic resonance imaging (MRI) data, camera data, and the like. Idealized model data can include idealized models of anatomical structure, including, but not limited to, major organs (heart, lungs, liver, kidneys, brain, etc.), joints, bone structure, musculature, chest cavity, the vascular system, central and peripheral venous systems, the cardiopulmonary system, the lymphatic system, the hepatic system, the renal system, the head and specifically the brain, sinuses, etc. and/or medical devices used in medical procedures including, but not limited to, implants, heart valves, embolic protection devices, stents, grafts, medical instruments, cardiac rhythm management devices, pacemakers, implantable cardioverter defibrillators, cardiac resynchronization therapy devices, ventricular assist devices, and the like. Idealized model data can be stored in CAD file formats including information regarding geometry (wireframe, surface, solid, etc.) or can be stored in other file formats including similar information about the idealized models.

As described above, systems for displaying visual information in three dimensions are typically based on mechanism for providing a first image to one eye of a user and a second image, different than the first, to a second eye of the user. In this manner, the image, as perceived by the user can appear to have depth and therefore appear to be in three-dimensional. In some cases, a separate video image can be provided to each eye of a user through separate video screens or separate portions of a single video screen. In other cases, the separate video screens can be disposed within a headset or glasses.

However, in some cases, a single video screen can be used in combination with a technique to allow each eye to see different aspects of the screen, such as with polarized eyewear. In some embodiments, a stereoscopic image including a left image and a right image that is spatially multiplexed within the stereoscopic image can be presented to a left eye and a right eye respectively of the user of a left polarizing filter and a right polarizing filter. An exemplary approach of this type is described in US 2007/0043466, the content of which is herein incorporated by reference.

It will be appreciated that systems herein can have various form factors in order to provide a user interface including a view of a three-dimensional model of a patient's anatomy. By way of example, the system can include a headset with one or more screens to show separate images to the left and right eye, a screen with a multiplexed left and right image and glasses to cause the left eye to see the left image and the right eye to see the right image, or a similar system. In some embodiments the system can include sensors so as to track the position of a user's head. One approach for tracking the position of a user's head is described in US 2013/0128011, the content of which is herein incorporated by reference.

In some embodiments, the system can be configured to allow a leader (or primary user) can switch between their own perspective view and a mirrored perspective view of a particular secondary user. For example, in the context of a teacher or expert presenting information to others, it can be useful for the teacher or expert to snap to the current view of a particular student or other participant. By doing so, the teacher or expert can immediately observe precisely what the student or other participant is currently viewing and from what distance, angle, etc. This can be useful in order to gauge (or track and assess) the understanding of the student or other participant. This can also be useful if the student or other participant has asked a question so that the teacher or expert can more fully understand what is being asked and the reason for the question. This can be implemented in various ways. In some embodiments, information that identifies the current perspective of other users (such as secondary users) is broadcast within the network of individuals viewing the same three-dimensional model. For example, the individuals viewing the same three-dimensional model can be in data communication through a data network (packet switched or an alternative approach). The information can be broadcast through a communications circuit. This information can include coordinates, viewing angles, degrees of rotation, depth, etc. The teacher or expert can select a particular user and enter a command (such as by actuating a command interface object) which causes their own machine or video rendering system to change their currently displayed perspective on the three-dimensional model to match that of the selected user.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit, the primary user interface can include a three-dimensional model of at least a portion of a subject's anatomy from a first perspective. The first perspective can be configured to be controlled by a primary user.

The primary user interface can also include a command interface object, wherein engagement of the command interface object causes the primary user's interface to begin mirroring the perspective of the secondary user on the three-dimensional model of the subject's anatomy. In some embodiments, engagement of the command interface object can also cause the primary user's interface to begin controlling the perspective of the secondary user on the three-dimensional model of the subject's anatomy.

In some embodiments, the command interface object(s) can be a graphical button, such as button 512 as shown in FIG. 5. In other embodiments, the command interface objects can take on other forms such as a right-click context menu item, a menu tree command, a keyboard command, a drop-down menu item, or another type of user interface object.

In some embodiments, the leader can cause the view of one or more particular secondary user(s) to switch between the secondary user's current perspective view and a mirrored view of the leader's current perspective view. For example, in the context of a teacher or expert presenting information to others, it can be useful for the teacher to cause one or more students or other participants to simultaneously view what the teacher is currently viewing. By doing so, the teacher or expert can interface with the system in order to show an aspect or perspective of the three-dimensional model of the subject's anatomy that holds significance for a point to be made and then cause that same aspect or perspective to be mirrored to the views of one or more students or other participants.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit, the primary user interface including a three-dimensional model of at least a portion of a subject's anatomy from a first perspective, the first perspective configured to be controlled by a primary user.

The primary user interface can also include a command interface object, wherein engagement of the command interface object causes a secondary user interface to begin mirroring the perspective of the primary user on the three-dimensional model of the subject's anatomy.

This functionality can be implemented in various ways. In some embodiments, information that identifies the current perspective or a leader or primary user can be broadcast within the network of individuals viewing the same three-dimensional model. This information can include coordinates, viewing angles, degrees of rotation, depth, etc. The information can be broadcast continuously, periodically, on demand, or the like. The leader or primary user can select one or more users and enter a command (such as by actuating a command interface object) which causes those selected user's machines or video rendering systems to change their currently displayed perspective on the three-dimensional model to match that of the leader or primary user.

In some embodiments, the command interface object(s) can be a graphical button, such as button 512 as shown in FIG. 5. In other embodiments, the command interface objects can take on other forms such as a right-click context menu item, a menu tree command, a keyboard command, a drop-down menu item, or another type of user interface object.

In some embodiments, the primary user or leader can delegate control of a session to a secondary user or follower. An example includes where the leader wants a particular follower to walk through a scenario for the whole group.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit, the primary user interface including a three-dimensional model of at least a portion of a subject's anatomy from a first perspective, the first perspective configured to be controlled by a primary user.

The primary user interface can also include a command interface object, wherein engagement of the command interface object allows the primary user to select one out of a group of secondary users, wherein the selected secondary user gains the ability to direct the perspective on the three-dimensional model viewed by the primary user and/or one or more other secondary users.

This functionality can be implemented in various ways. In some embodiments, information that identifies the current perspective one or more secondary user(s) can be broadcast within the network of individuals viewing the same three-dimensional model. This information can include coordinates, viewing angles, degrees of rotation, depth, etc. The information can be broadcast continuously, periodically, on demand, or the like. The leader or primary user can select another user and enter a command (such as by actuating a command interface object) which causes other user's machines or video rendering systems to change their currently displayed perspective on the three-dimensional model to match that of the selected user.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a primary user. The method can further include displaying one or more command interface object(s), wherein engagement of the command interface object allows the primary user to select one out of a group of secondary users, wherein the selected secondary user gains the ability to direct the perspective on the three-dimensional model viewed by the primary user and/or one or more other secondary users.

In some embodiments, the leader can view the current position and/or perspective of one or more secondary user(s) without the one or more secondary users being able to see the positions of each other respectively. For example, in some scenarios, it can be desirable for a primary user or leader to be able to view the current positions and/or perspectives of all of the secondary users or other positions, but not have the secondary users see each other's positions. For example, if the primary user wanted to test the understanding of the secondary users, they could direct the secondary users to find a particular anatomical reference point and/or perspective on the same. It would then be desirable to be able to see if the second users were then able to successfully execute on the request.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit, the primary user interface including a three-dimensional model of at least a portion of a subject's anatomy from a first perspective, the first perspective configured to be controlled by a primary user.

The primary user interface can also include one or more graphical user representations of one or more secondary users who are viewing the same three or more dimensional graphical representation, wherein each of the one or more graphical user representations are not visible to the one or more secondary users. Information regarding the current perspective of users including, for example, coordinates, viewing angles, degrees of rotation, depth, etc. can be broadcast continuously, periodically, on demand, or the like. This information can be used by the rendering system of the primary user to display information regarding the perspectives other users in a graphical manner, a textual manner, or a combination of both.

The primary user interface can also include a command interface object, wherein engagement of the command interface object causes the graphical user representations of one or more secondary users to appear, disappear, or otherwise change.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a primary user. The method can further include displaying one or more graphical user representations of one or more secondary users who are viewing the same three or more dimensional graphical representation, wherein each of the one or more graphical user representations are not visible to the one or more secondary users. The method can include broadcasting (continuously, periodically, on demand, or the like) information regarding the current perspective of users including, for example, coordinates, viewing angles, degrees of rotation, depth, etc. This information can be used by the rendering system of the primary user to display information regarding the perspectives other users in a graphical manner, a textual manner, or a combination of both.

In some embodiments, the leader or primary user can put secondary users or other users into groups and then control aspects about the other users' interfaces at a group-level instead of individually.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit. The system can also include one or more secondary user interfaces generated by one or more secondary video processing circuits, each of the secondary user interface including a three-dimensional model of at least a portion of a subject's anatomy from a first perspective. The system can also include one or more secondary user interfaces generated by one or more secondary video processing circuits, each of the secondary user interface including a three-dimensional model of at least a portion of a subject's anatomy from a first perspective.

In some embodiments, the primary user interface can include a command function object, wherein selection of one or more secondary users and engagement of the command function object causes a user-group to be formed. In some embodiments, the selection of one or more secondary users can be made before engagement of the command function object. In some embodiments, the selection of one or more secondary users can be made after engagement of the command function object.

In some embodiments, after a group of secondary users is created, the primary user interface can allow the primary user to provide interface settings at a group-level.

In some embodiments, the system can include a messaging element to provide a message from a primary user or leader to a one or more secondary users or followers. Such messages can be provided visually through the user interface of the secondary user or follower.

In an embodiment, a distributed interactive medical visualization system is included, the system having a first video processing circuit, a first central processing circuit in communication with the first video processing circuit, and a first communications circuit in communication with the first central processing circuit. The system can also include a primary user interface generated by the first video processing circuit, the primary user interface including a three-dimensional model of at least a portion of a subject's anatomy from a first perspective, the first perspective configured to be controlled by a primary user.

The primary user interface can also include a command interface object, wherein engagement of the command interface object allows the primary user to create a communication for one or more secondary users. Engagement of a command interface object can then cause the communication to be broadcast and displayed on one or more secondary user interfaces.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a primary user. The method can further include displaying one or more command interface object(s), wherein engagement of the command interface object allows the primary user to create a communication for one or more secondary users. Engagement of a command interface object can then cause the communication to be broadcast and displayed on one or more secondary user interfaces.

It will be appreciated that the operations included in methods herein are not limited to a particular progression of events unless otherwise noted. Any progression is appropriate that allows the technology discussed herein to be realized.

In some embodiments, the invention includes a device including a graphical display and a machine-readable medium comprising instructions. The instructions can perform various operations when implemented by one or more processors. By way of example, the operations can include those in accordance with methods as described herein. The machine-readable medium can include random access memory (RAM), read-only memory (ROM), magnetic data storage media, optical data storage media, flash memory, and the like.

Figure 8:
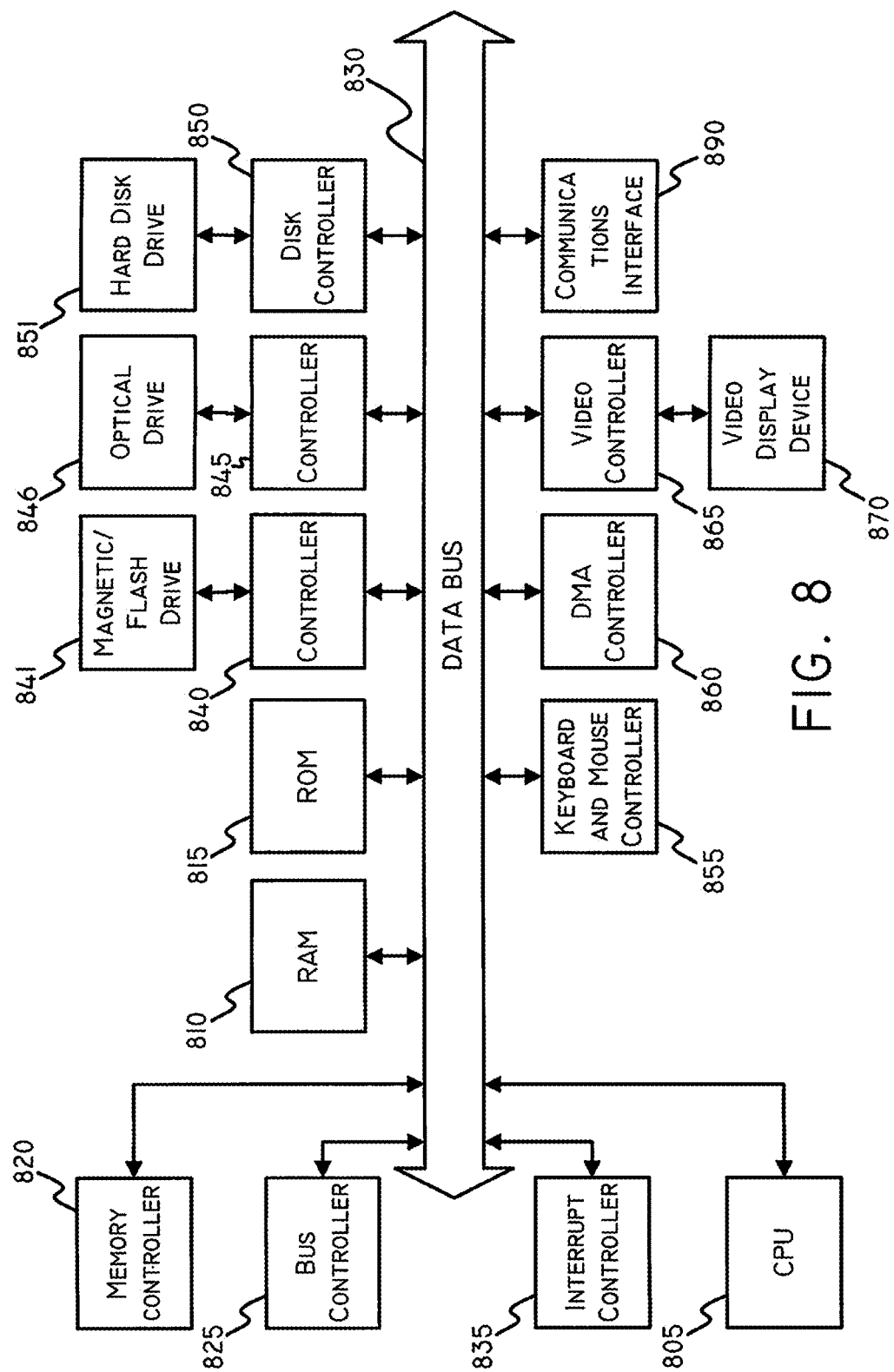
FIG. 8 is a diagram of various components in accordance with some embodiments herein.

Devices to display three-dimensional models of at least a portion of a subject's anatomy and/or user interfaces for the same can include components common to many computing devices. Referring now to FIG. 8, a diagram of various components is shown in accordance with some embodiments. The system can include a central processing circuit that can include various components such as a central processing unit. By way of example, the system can include a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by a magnetic or flash memory drive 841 including removable or non-removable media, which is connected to bus 830 by controller 840, an optical drive such as CD-ROM or DVD drive 846, which is connected to bus 830 by controller 845, and/or hard disk drive 851 (magnetic or solid state), which is connected to bus 830 by controller 850. In some embodiments, mass storage can be provided by a device connected through a universal serial bus (USB), eSATA, FireWire, or Thunderbolt interface or other type of connection. User input to the programmer system may be provided by a number of devices. For example, a keyboard and mouse can be connected to bus 830 by keyboard and mouse controller 855. DMA controller 860 is provided for performing direct memory access to system RAM 810. In some embodiments user input can be provided by a pen, light pen, glove, wearable object, gesture control interface, or the like.

A video processing circuit can be included and can generate a user interface. The video processing circuit can include a video controller 865 or video output, which controls video display 870. In some embodiments, the video controller 865 can also include one or more graphical processing units (GPUs). The video processing circuit can be in communication with the central processing circuit.

The system can also include a communications interface 890 or communications circuit which allows the system to interface and exchange data with other systems and/or servers. The communications circuit can be in communication with the central processing circuit. In some embodiments, the communications interface 890 can include a network interface card or circuit to facilitate communication with a packet switched (such as IP) or other type of data network.

It will be appreciated that some embodiments may lack various elements illustrated in FIG. 8. In addition, the architecture shown in FIG. 8 is merely one example of how discrete components can be arranged and other architectures are explicitly contemplated herein.

In addition to, or instead of, the components described with respect to FIG. 8, it will be appreciated that the system can also include a microcontroller, a programmable logic controller (PLC), an ASIC, an FPGA, a microprocessor, or other suitable technology.

The video processing circuit (either locally or on a remote node) can generate a 3D (or fewer or more dimensions) image based on information including one or more of geometry, viewpoint, texture, lighting and shading information, and other information described above. In some embodiments, information for rendering an image is combined within a scene file. The term "graphics pipeline" can be used to refer to the sequence of steps used to create a 2D raster representation of a 3D scene. The video processing circuit can execute one or more steps of the graphics pipeline. The video processing circuit can also include one or more physical components used in the graphics pipeline. Using the information described above, the graphics pipeline can include one or more stages of creating a scene out of geometric primitives, modelling and transformation, camera transformation, lighting, projection transformation, clipping, scan conversion or rasterization, and texturing and fragment shading. In various embodiments, other operations can also be performed. In various embodiments, the graphics pipeline can use OpenGL, DirectX, or other protocols.

Figure 9:
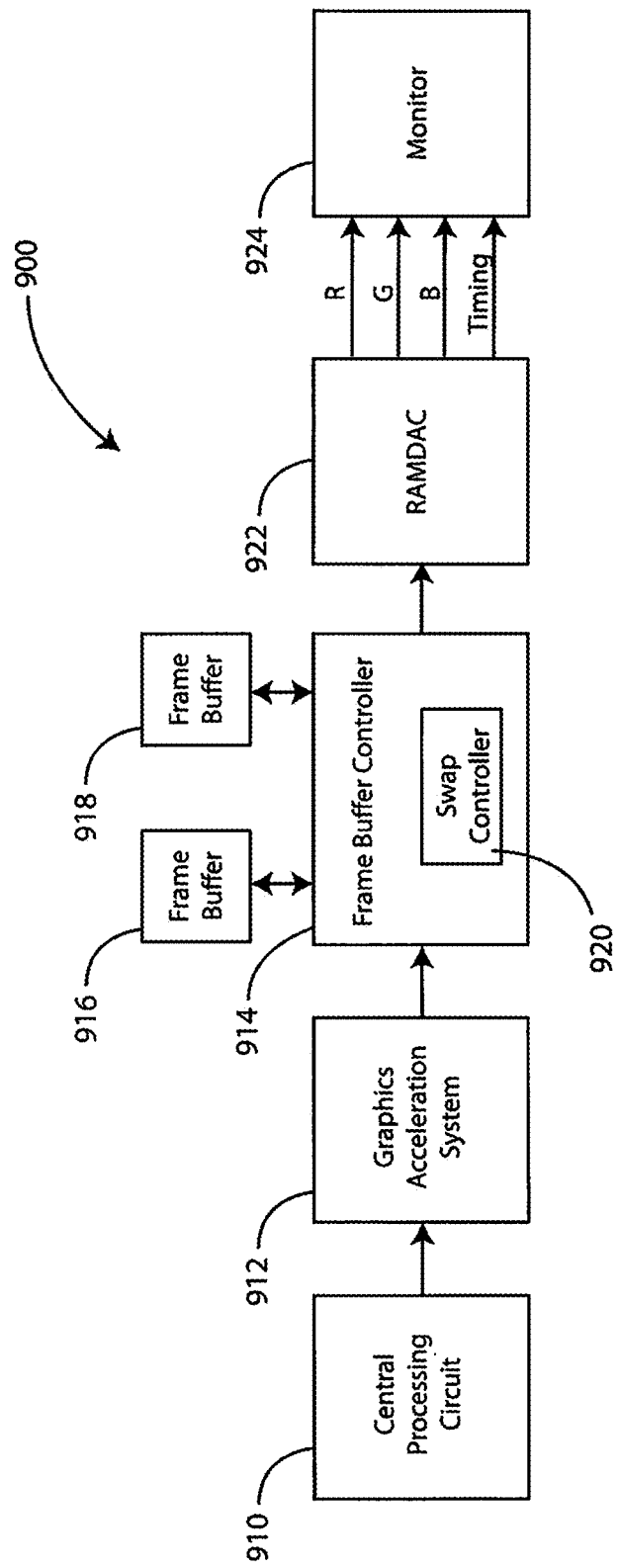
FIG. 9 is a diagram of various components of an exemplary graphics pipeline in accordance with various embodiments herein.

It will be appreciated that various forms of graphics pipelines can be used. As just one example, an exemplary computer graphics pipeline 900 is shown in FIG. 9. In this example, a host computing system or central processing circuit 910 (which can be local or on a remote node) runs system and application software that is capable of modeling a scene in terms of polygon vertices, color, lighting, textures and so on. The central processing circuit 910 sends this information to graphics acceleration system 912 (which can be local or on a remote node). Graphics acceleration system 912 can render the modeled scene by generating pixel data for storage in a frame buffer memory. The contents of the frame buffer memory can be continually read by a random access memory/digital-to-analog converter ("RAMDAC") module 922 which typically contains color or gamma correction lookup tables and drives a display monitor 924. Alternatively, central processing circuit 910 may generate the pixel data without a graphics acceleration system and write the pixel data into the frame buffer directly.

In some cases, a technique known as double buffering can be used. In double buffering, two frame buffers 916 and 918 are provided instead of a single frame buffer. In this manner, the central processing circuit 910 or graphics acceleration system 912 can write pixel data into one frame buffer (the "non-viewable" or "back" buffer) while RAMDAC module 922 and monitor 924 display pixel data previously written into the other frame buffer (the "viewable" or "front" buffer). The effect of this technique is to reduce tearing and other unwanted visual artifacts that are introduced into an image when the contents of a frame buffer are changed while the contents of the same frame buffer are being displayed. In systems that use two buffers, a frame buffer controller 914 can be used to coordinate which buffer will be viewable and which will be non-viewable at any given moment. Specifically, a swap controller 920 within frame buffer controller 914 can indicate when it is safe to stop displaying the contents of one frame buffer and to start displaying the contents of the other frame buffer. Typically, swap controller 920 will indicate that it is safe to swap frame buffers at the moment when (1) the graphics pipeline has finished rendering pixel data into the non-viewable buffer, and (2) the current raster position of the display is not within the window of interest. In full screen graphics, buffer swapping normally occurs only during a vertical retrace, however it can be performed at various times. In windowed graphics, buffer swapping might occur at any time when the raster is not within the window of interest.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A distributed interactive medical visualization system comprising:
    a first video processing circuit;
    a first central processing circuit in communication with the first video processing circuit;
    a first communications circuit in communication with the first central processing circuit;
    a primary user interface generated by the first video processing circuit, the primary user interface including
        a three-dimensional model of at least a portion of a subject's anatomy from a first perspective, the first perspective configured to be controlled by a primary user, and
        a user input enabling interaction with the three-dimensional model by the primary user;
    a secondary user interface configured to be controlled by a secondary user, the secondary user interface displaying the three-dimensional model from a second perspective, the secondary user interface comprising a user input enabling interaction with the three-dimensional model by the secondary user;
    a command interface object displayed on the primary user interface, wherein engagement of the command interface object by the primary user via the user input of the primary user interface causes the secondary user interface to begin mirroring the first perspective of the primary user on the three-dimensional model of the subject's anatomy on the secondary user interface.

2. The distributed interactive medical visualization system of claim 1, the three-dimensional model including one or more of patient data gathered in real-time, previously stored patient data, and idealized model data.

3. The distributed interactive medical visualization system of claim 1, wherein information about the current perspective of the primary user is broadcast across a network.

4. The distributed interactive medical visualization system of claim 1, wherein information about the current perspective of the secondary user is broadcast across a network.

5. The distributed interactive medical visualization system of claim 1, wherein the first video processing circuit is co-located with a machine displaying the primary user interface.

6. The distributed interactive medical visualization system of claim 1, wherein the first video processing circuit is remotely located from a machine displaying the primary user interface.

7. A distributed interactive medical visualization system comprising:
    a first video processing circuit;
    a first central processing circuit in communication with the first video processing circuit;
    a first communications circuit in communication with the first central processing circuit;
    a primary user interface generated by the first video processing circuit, the primary user interface including
        a three-dimensional model of at least a portion of a subject's anatomy from a first perspective, the first perspective configured to be controlled by a primary user, and
        a user input enabling interaction with the three-dimensional model by the primary user;
    a secondary user interface displaying the three-dimensional model from a second perspective, wherein a secondary user can change the second perspective of the three-dimensional model of the subject's anatomy, the secondary user interface comprising a user input enabling interaction with the three-dimensional model by the secondary user;
    a command interface object on the primary user interface, wherein engagement of the command interface object by the primary user via the user input of the primary user interface causes the primary user interface to display the three-dimensional model of the subject's anatomy from the second perspective in a mirrored fashion.

8. The distributed interactive medical visualization system of claim 7, the three-dimensional model including one or more of patient data gathered in real-time, previously stored patient data, and idealized model data.

9. The distributed interactive medical visualization system of claim 7, wherein information about the current perspective of the primary user is broadcast across a network.

10. The distributed interactive medical visualization system of claim 7, wherein information about the current perspective of the secondary user is broadcast across a network.

11. The distributed interactive medical visualization system of claim 7, wherein the first video processing circuit is co-located with a machine displaying the primary user interface.

12. The distributed interactive medical visualization system of claim 7, wherein the first video processing circuit is remotely located from a machine displaying the primary user interface.

13. A distributed interactive medical visualization system comprising:
- a first video processing circuit;
- a first central processing circuit in communication with the first video processing circuit;
- a first communications circuit in communication with the first central processing circuit;
- a primary user interface generated by the first video processing circuit, the primary user interface including
  - a three or more dimensional graphical representation of at least a portion of a subject's anatomy from a first perspective, the primary perspective configured to be controlled by a primary user, and
  - a user input enabling interaction with the three-dimensional model by the primary user;
- a plurality of secondary user interfaces each comprising a user input enabling interaction with the three-dimensional model by a secondary user, each secondary user interface displaying the three-dimensional model, wherein a secondary user of each secondary user interface can change a perspective of the three-dimensional model of the subject's anatomy via the secondary user input;
- a plurality of graphical user representations displayed on the primary user interface, each graphical user representation representing a respective position and current view of a secondary user who is interacting with the same three or more dimensional graphical representation on a secondary user interface, wherein each of the one or more graphical user representations are not visible on the one or more secondary user interfaces.

14. The distributed interactive medical visualization system of claim 13, the three or more dimensional graphical representation including one or more of patient data gathered in real-time, previously stored patient data, and idealized model data.

15. The distributed interactive medical visualization system of claim 13, wherein information about the current perspective of the primary user is broadcast across a network.

16. The distributed interactive medical visualization system of claim 13, wherein information about the current perspective of a secondary user is broadcast across a network.

17. The distributed interactive medical visualization system of claim 13, the primary user interface including a command function object, wherein selection of a one or more secondary users and engagement of the command function object causes a user-group to be formed; the primary user interface allowing the primary user to specify interface settings at a group-level.

18. The distributed interactive medical visualization system of claim 13, the primary user interface including a command interface object, wherein engagement of the command interface object allows the primary user to select one out of a group of secondary users, wherein the selected secondary user gains the ability to direct the perspective on the three or more dimensional graphical representation viewed by the primary user and the other secondary users.

19. The distributed interactive medical visualization system of claim 13, the primary user interface including a command interface object, wherein engagement of the command interface object allows the primary user to create a communication for one or more secondary users to be displayed on one or more secondary user interfaces.

20. The distributed interactive medical visualization system of claim 13, the three or more dimensional graphical representation of at least a portion of a subject's anatomy including one or more of patient data gathered in real-time, previously stored patient data, and idealized model data.

* * * * *